United States Patent [19]

Bäthmann et al.

[11] Patent Number: 4,492,118

[45] Date of Patent: Jan. 8, 1985

[54] NONDESTRUCTIVE TESTING OF STRUCTURAL MATERIAL BY MEANS OF ULTRASONICS

[75] Inventors: Hans-Jürgen Bäthmann, Moers; Bernhard Hoh, Hünxe; Siegmar Schulz, Cologne, all of Fed. Rep. of Germany

[73] Assignees: Mannesmann AG, Duesseldorf; Krautkraemer GmbH, Cologne, both of Fed. Rep. of Germany

[21] Appl. No.: 415,830

[22] Filed: Sep. 8, 1982

[30] Foreign Application Priority Data

Sep. 8, 1981 [DE] Fed. Rep. of Germany ....... 3135969

[51] Int. Cl.³ ............................................. G01N 29/04
[52] U.S. Cl. ......................................... 73/612; 73/611
[58] Field of Search ................. 73/615, 612, 610, 611, 73/614

[56] References Cited

U.S. PATENT DOCUMENTS 3,872,715  3/1975  Pittaro ............................. 73/612 X
4,147,065  4/1979  Lather et al. ..................... 73/615 X Primary Examiner—Charles A. Ruehl
Attorney, Agent, or Firm—Ralf H. Siegemund

[57] ABSTRACT

Plate stock of uneven and variable thickness is tested for defects by means of ultrasonics whereby the zone adjacent the front surface and up to a depth of the minimum plate thickness is detected conventionally, but under utilization of a novel method the zone of variable thickness adjacent the rear wall is tested by detecting any echo in a gating period (15) that is returned from that zone or from the rear wall, and such an echo is used to set up a supplemental gating period during which either none or the rear wall echo will occur and in the latter case the setting up of the supplemental gating period is interpreted as having resulted from the presence of a defect (for example, echo 12) so that the occurrence of the rear wall echo 9 within the supplemental gating period is registered as an indication of a defect.

5 Claims, 6 Drawing Figures

NONDESTRUCTIVE TESTING OF STRUCTURAL MATERIAL BY MEANS OF ULTRASONICS

BACKGROUND OF THE INVENTION

The present invention relates to ultrasonic testing of structural materials particularly of workpieces made of metal for the purposes of detecting internal flaws, defects, inclusions or the like.

Sheet and plate stock, for example, is tested by launching ultrasonic test pulses perpendicularly to one surface and by searching for reflections of the ultrasonic signal, for example, by a defect. The sheet stock or plate may be so tested in its entirety and progressively over one surface thereby covering the entire interior of the stock. The return signals are usually processed by restricting the detection of echoes which occur within a certain period of time only because other echoes are deemed to have causes other than defects. Typically, for example, the so called rear wall echo will always occur as the result of the reflection o the ultrasonic pulse by the surface opposite the surface into which the test pulse was launched. In the case of a uniform wall thickness (i.e., in the case of sheet and plate stock of a uniform thickness) the time between the launching of the pulse into the workpiece and the occurrence of the rearwall echo is quite constant. Therefore, the period of time within which to look for echoes from defects in the interior of the workpiece is well defined. The situation is different, however, when the wall thickness varies intentionally or otherwise. In such a case, one has to consider the minimum wall thickness as the criteria defining rear wall echo timing and any echo that occurs after the minimum period has elapsed will be suppressed. This means that a portion of the sheet stock in locations where the wall thickness exceeds the minimum will not be tested. Alternatively, one can detect any echo whenever it occurs and evaluate the total transit time to thereby exclude detected rearwall echoes from echoes resulting from defects. The problem could be solved, for example, through follow-up systems in which in very small steps and on a progressive basis one keeps track of the rearwall echoes to thereby delineate the wall thickness, and echoes occurring within the variable period delineating the wall thickness can then be interpreted as defects. However, tracking the actually occuring wall thickness just for that purpose is complicated and expensive. Moreover, this matter requires a high resolution pattern for testing the workpiece as a whole without actual improvement in test sensitivity. One has also tried to include so called jump detectors in which echoes of sequential test cycles are compared under the assumption that the wall thickness varies gradually, and in the case of a jump in transit time of echoes that jump is interpreted as a defect. However, this is not a reliable method and in fact nonexisting "defects" may be indicated.

DESCRIPTION OF THE INVENTION

It is an object of the present invention to provide a new and improved method and equipment for nondestructive testing of structural material such as plate stock or the like having front and rear surfaces, but a nonuniform thickness under utilization of ultrasonic test pulses which are set into the front surface and under further ultilization of echoes which are being detected, converted into electrical signals and processed further.

It is another object of the present invention to provide a new and improved method for nondestructive reproducible testing of structural material and workpieces of variable thickness under utilization of equipment which in the past permitted merely testing of zones within the material equal to minimal wall thickness.

In accordance with the preferred embodiment of the present invention, a first gating and signal detection period is provided for echo signals which covers at least a period in which a rear wall echo signal will appear; any echo signal which occurs within that first gating period is detected. Such an echo signal may be a defect echo or a rear wall echo, in either case this detection is used for generating a second gating and detection period; and finally a rear wall echo is detected, if it occurs in the second gating period as an indication of the presence of a defect.

It can thus be seen that the principal behind the invention is the intentional extension of a detection period for searching additionally for further away defects, but also for the rear wall echo. If an echo occurs within this preliminary detection period it cannot per se be identified as a defect echo or a rear wall echo but is used for the setting up of a further detection period. If no echo occurs within this supplemental detection period then the previously detected echo was the rear wall echo. If, however, within the supplemental detection period another echo (i.e., from the true rear wall) occurs then the previous echo was generated by reflection from a defect. That defect now is indicated indirectly by the supplemental detection of the rear wall echo. Moreover, it can readily be seen that the principal of the invention involves supplementing the existing circuitry such as ultrasonic test equipment whose use was previously restricted to the detection of flaws within the minimal wall thickness zone behind the front surface through which the test pulses are launched. The inventive principal extends the detection range further by means of equipment which simply can be added on to existing equipment. The original detection period should remain separate; the extension of detection covers the transit time equivalents of rear wall echoes of minimum and maximum thickness portions. The supplemental detection period is preferably equal in length to the extension period.

DESCRIPTION OF THE DRAWINGS

While the specification concludes with claims, particularly pointing out and distinctly claiming the subject matter which is regarded as the invention, it is believed that the invention, the objects and features of the invention, and further objects, features and advantages thereof, will be better understood from the following description taken in connection with the accompanying drawings, in which:

Proceeding now to the detailed description of the drawing, FIG. 1 illustrates a piece of generally flat stock 1 having, however, variable wall thickness as represented here by an indent. The stock is nondestructively tested by ultrasonic test equipment which includes a test head 2 launching ultrasonic pulses into the material, possibly via a water column that bridges the physical input and output of the test head 2 with the solid material of which the workpiece 1 is made. The ultrasonic pulse launched by the test head 2 traverses the surface 3 of the workpiece 1 at right angles thereto. The test pulse propagates through the material and is reflected in part by the opposite surface 4 and returns as an echo signal into the test head 2 which in the meantime, for example, has been switched over from a transmitter mode to a receiver mode.

It can readily be seen that in the position A of the testhead, the rear wall echo occurs relatively late. In the position B, however, the rear wall echo occurs significantly earlier. If one now assumes that the stock thickness and the bottom of the indent defines the minimum wall thickness of the sheet stock, the minimum being established by the level 5, and if one assumes further that echo detection by itself is restricted to echos occurring prior to the earliest possible rear wall echo (this condition exists as position B) then one can see that in the position C the defect 6 will not be detected for the following reasons. The echo produced by the defect 6 occurs at a time that is earlier than the true rear wall echo will occur, namely a reflection on surface portion 4 when the testhead is in position C. However, the rule according to which rear wall echoes are to be excluded from the detection sequence, requires in turn that the test equipment be desensitized for periods after the earliest possible rear wall echo could have occured which is of course determined by the minimum wall thickness level 5. A defect situated in the material between that minimum wall thickness level 5, on one hand, and the true rear surface of the material to be tested will not be detected.

Figure 1:
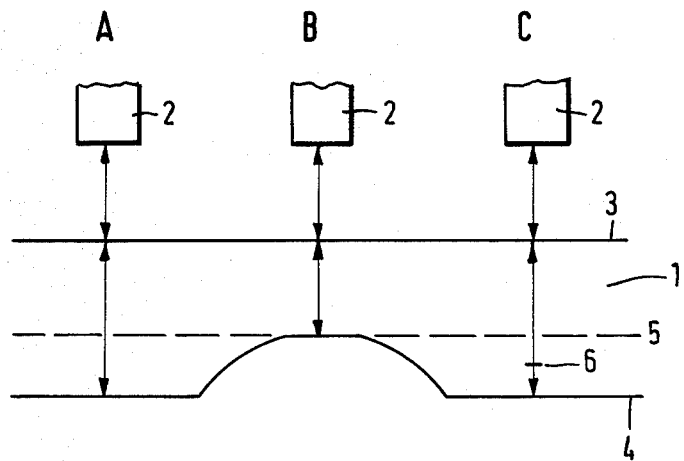
FIG. 1 illustrates somewhat schematically ultrasonic testing of a piece of stock of variable thickness.
Figure 2:
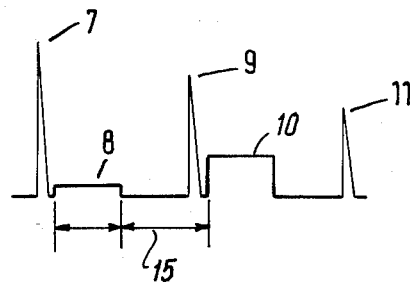
FIGS. 2, 3, and 4 are pulse-time diagrams derivable from and pursuant to testing as illustrated in FIG. 1 in three different relative positions of the test head vis-a-vis the test stock.
Figure 3:
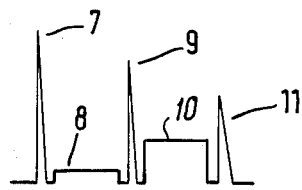
Figure 4:
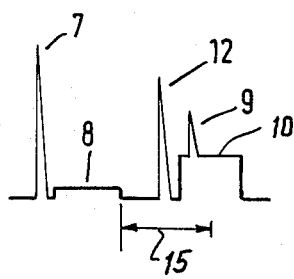

Turning briefly to the timing diagrams of FIGS. 2, 3, and 4 it will suffice for the moment that the pulse diagram of FIG. 2 pertains to the position A of the testhead in FIG. 1. Typically, there will be a front wall or entrance echo 7 which follows immediately the launch, after the transmitted ultrasonic signal has traversed the distance between the testhead and the front surface 3. Reference numeral 8 delineates the range within which defect echoes are to be detected. A certain period thereafter elapses until the rear wall echo 9 arrives. At a somewhat later time, a second rear wall echo 11 arrives resulting from a reflection of the first rear wall echo in parts on the surface 3, back into the material and again by surface 4.

FIG. 3 illustrates an analogous pulse and timing diagram but for the position B of the testhead 2 and here one can see that the rear wall echo 9 appears immediately after the end of the detection interval 8. The timing distance or spacing between the two echo peaks 7 and 9 for this particular case defines, in terms of transit time difference, the minimum wall thickness which represents the restricted detection interwall. One can readily see that in the diagram of FIG. 4 the wall thickness has its normal value, but an echo peak 12 results from the reflection of the test pulse by the flaw or defect 6. That particular pulse will not be detected within the detection interval 8. We will return to these figures after explaining in detail the effect and operation of the inventive circuit which remedies the situation and makes it possible that a defect such as 6 will in fact be detected.

Briefly, the principle behind the invention is to use any echo that subsequently to the regular detection interval 8 to open up another looking window and detection period. If a rear wall echo occurs within that particular supplemental period, then the pulse which was detected previously and gave rise to the setting up of this supplemental detection period and looking window was a defect echo; if no echo occurs within the supplemental detection period and looking window then the pulse which resulted in the last mentioned setup was in fact the rear wall echo and there is no defect within the zone defined by the minimum wall thickness and the actual wall thickness.

Figure 5:
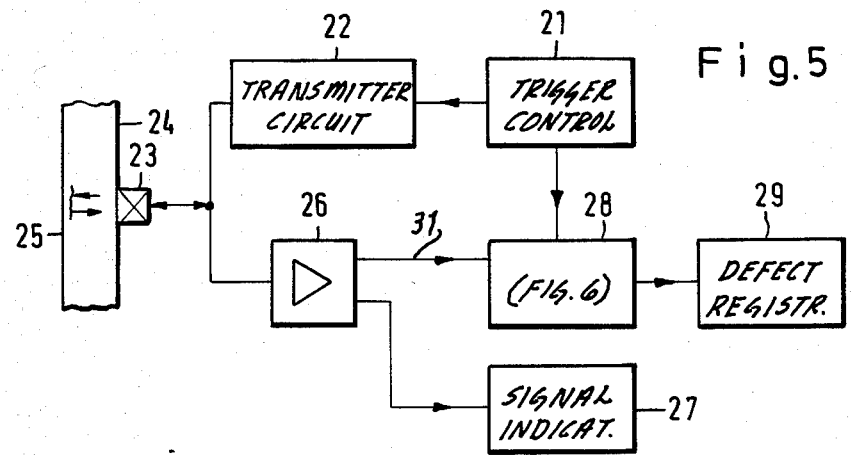
FIG. 5 is a block diagram of a test system that incorporates an example of the preferred embodiment of the invention for practicing the best mode thereof.

Proceeding now to the description of FIG. 5, a test piece such as a piece of plate stock of a conceivably irregular wall thickness is nondestructively tested by ultrasonic test pulses using a testhead 23 being suitably coupled to the surface of the workpiece and in progressive portions thereto. The test piece has a front wall 24 and a rear wall 25. The testhead serves as a transmitter for ultrasonic pulses as well as receiver in alternating transmit and receive cycles, a pair of such cycles constituting a test cycle. The circuit accordingly has a transmit or transmitter branch and a receiver branch. The transmitter branch includes a trigger circuit 21 which may be suitably computer controlled in accordance with the particular test program and a timing operation commensurate with a test task at hand. That particular circuit 21 issues trigger pulses to a transmitter 22 proper, which provides a contoured signal for purposes of triggering and stimulating the transmitter portion of the transducer 23 for purposes of launching an ultrasonic test pulse into the test piece through the front wall 24. A representative example of a defect is shown near the rear wall. Ultrasonic pulses reflected for any reason including front and rear wall echoes as well as echoes on defects as they may occur, are returned into the transducer head 23 then being operated in the receiver mode and converting the ultrasonic vibrations it receives into an electrical signal to be passed on to a suitable amplifier 26. The circuit 26 may be comprised of several stages and has accordingly, for purposes of impedance matching or the like, different output branches. One output circuit of the amplifier 26 leads to a display monitor 27, but that is not essential as far as practicing the invention is concerned. The second output branch 31 of amplifier 26 leads to a circuit 28 to be described in greater detail below with reference to FIG. 6 and including several gating circuits. These gating circuits are cyclically operated to some extent in response to particular signals derived from the amplifier 26, but the detection cycle for each test cycle begins with a trigger pulse which is, of course, derived from the trigger circuit 21. Reference numeral 29 refers generally to a flaw or defect indicating or registering device which in a more simple form may simply signal absence and presence of a defect signal, but the circuit 29 can be a bit more involved in nature and may include electronic processing and storage of signals representing defects in order to work a redundancy control etc.

Figure 6:
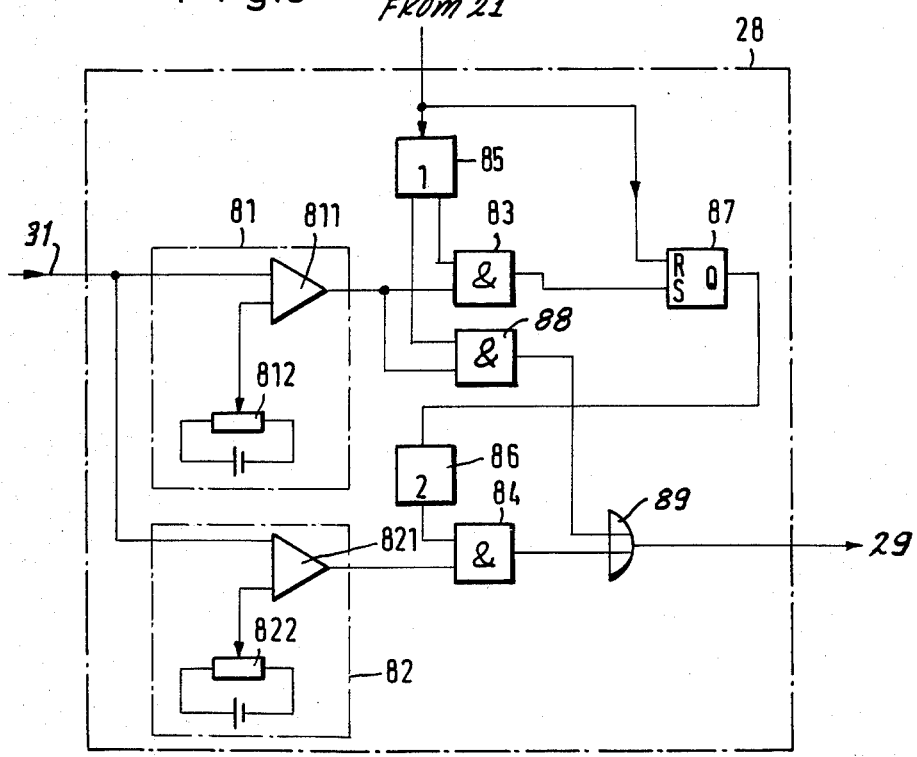
FIG. 6 is a more detailed diagram of a relevant component shown in FIG. 5.

The particular gate circuit shown in FIG. 6 includes an input line 31 from which measuring signals are derived from amplifier 26 in FIG. 5. The signal is to some extent free from noise as can be obtained through proper response and threshold adjustment in amplifier 26, but basically the signals that arrive in line 31, are comprised of echoes that have been returned by the reflecting surfaces in the test piece.

The circuit 28 is comprised of two threshold circuits 81 and 82 each receiving the test signal from line 31 and each including a comparator or differential amplifier being denoted 811, and 821 respectively for the two circuits 81 and 82; the line 31 being accordingly connected to one input each of these two comparators. The second input of each of these comparators receives reference signals, from the circuits 812, and 822 respectively, which are individually adjustable in order to adjust the response level for the two threshold circuits 81 and 82 to different levels. For reasons below, it can be seen that the threshold adjusted by the circuit 812 for the circuit 811 is lower, possibly considerably lower, than the threshold adjusted by means of circuit 822 for the comparator 821. The output of comparator 811 is fed to one input of a logic coincidence gate such as an AND gate 83 while the output of comparator 821 is fed to a similar AND gate 84.

AND gate 83 has a second input which can be regarded as an enabling signal or gating-open signal derived from a timing circuit 85. Circuit 85 receives a trigger signal from the circuit 21 being indicative of the beginning of a test cycle and of the launching of a new test pulse by the transmitter 23. The timing signal provided by circuit 85 to the AND gate 83 is an enabling signal of a particular duration which is indicated by reference numeral 15 in FIGS. 2 and 4. It is a timing signal which begins at an instant immediately succeeding the end of the detection period 8.

Period 8 covers the portion of the plate stock defined by the front surface through which ultrasonic test pulses are launched and the level representing the minimum plate stock thickness (level 5 in FIG. 1). The period 15 is metered by the circuit 85 for use in the and gate 83; it begins when period 8 ends, and ends for example, at an instant measured from the time of triggering (circuit 21) and elapsing after a rear wall echo will occur for a maximum plate stock thickness (see FIG. 2). The period 15 thus covers, in terms of a transit time range equivalent, the variation or differential between minimum and maximum plate thickness.

The immediate detection within the interval 8 is provided through a gate 88 receiving a second timing signal from circuit 85 that begins shortly after the trigger pulse 21 or more precisely shortly after the front wall echo (7 in FIGS. 2, 3, and 4) has decayed and it ends when the period 15 begins. Therefore, the And gate 88 is enabled during the period 8 (being in fact defined by this enabling state) and gate 88 with pass an output signal from the threshold device 81 which may occur as a result of a defect within the more frontal portion of the plate stock as defined. the gate 83 is enabled after gate 88 is disabled again and will pass subsequently occurring echo signals which, however, can be a rear wall echo or the echo from a defect such as 6 in FIG. 1. The output of AND gate 88 is fed to one input of an OR gate 89 whose output is fed to the defect indicator 29. The output of AND gate 83 is processed otherwise.

The trigger signal from circuit 21 is used in addition to reset a regular, set-reset type flip flop or latch 87. Any output signal from threshold circuit 81 that passes gate 83 is used to set the flip flop 87. The output of flip flop 87, particularly the set state or Q signal is used to trigger another timing circuit 86 which provides the *supplemental* time interval 10 (see FIGS. 2, 3, and 4). The output of 86 is also in the form of a suitable gating signal for the AND gate 84. That particularly timing signal begins shortly after the flip flop 87 has been set by an echo pulse from gate 83 and in order to wait for the completion of that particular echo signal that caused circuit 81 to respond and to pass through the AND gate 83 and trigger or set flip flop 87. The time interval period 10 as provided by the circuit 86 may be of a like duration as the time period 8 or, more appropriately, like the period 15. This timing and gating signal from circuit 86 is fed to the second input of the AND gate 84 whose first input receives the output of the comparator 821 as mentioned above. Therefore, the AND gate 84 constitutes a second input for the OR gate 89 and passes its output on to the circuit 29 as another alternative way of signaling the presence of a defect.

The circuit as described operates as follows during a particular test cycle. Circuit 21 provides a trigger pulse signal which begins a test cycle and that trigger signal gives rise to the launching of a ultrasonic test pulse by the transducer 23. In addition that trigger signal resets flip flop 87 and starts the timer 85. Shortly thereafter, the first timing signal is provided through the AND gate 88 and the detection period 8 thus begins.

If a defect exists in a more frontal portion of the plate stock being tested an echo signal will appear during this period 8 and will pass though AND gate 88 and OR gate 89 tube registered in 29. As stated above, the period 8 is selected such that a rear wall echo cannot possibly occur within that detection period because the minimum wall thickness is such that a rear wall echo of the thinest portion still will arise a little after the period 8 has elapsed. Now, however, timing circuit 85 provides another enabling signal to the AND gate 83 for detecting later occurring echoes during the period 15. The echo signal that occurs during 15 in the situation depicted in FIGS. 2 and 3 is the rear wall echo. The rear wall echo when detected sets the flip flop 87 and the timer 86 begins to run beginning shortly after that rear wall has decayed and the gate 84 is enabled for the period 10. In the cases of test positions A and B (FIGS. 2 and 3) no further pulses occur except a second rear wall echo at some later time, but that is delayed well beyond the expiration of supplemental detection period 10, therefore, no pulse passes gate 84 and a defect is not indicated.

The situation is different in position C the timing being shown in FIG. 4. Again it is assumed that no defect exists in the frontal portion of the material so that the period 8 expires uneventfully. In the now ensuing period 15 during which gate 83 is open an echo from defect 6 appears and passes through gate 83 to set the flip flop 87, and timing circuit 86 begins to furnish the detection interval 10 after this echo signal has decayed. the rear wall echo 9 will occur at some time thereafter. The rear wall echo 9 may pass also through the gate 83 which will still be open, but flip flop 87 is in the set state so that no further action occurs. The gate 88 is closed when the rear wall echo arrives so that the rear wall echo will not in fact go beyond the circuit 81–83. However, the rear wall echo is also fed to the comparator 821 of the threshold circuit 82. The threshold level for the comparator 821 may well be selected to be sufficiently high to suppress any other pulses except the relatively large rear wall echo. That output signal from the comparator 821 now passes the AND gate 84 and is fed through the OR gate 89 to the error detection circuit 29. The rear wall echo is used here as an indicator for the presence of a defect close to the rear wall of the plate stock to be tested. This way one does in fact detect the presence of defects in the zone which otherwise is excluded from the regular or normal detection carried out through the AND gate 88 as described.

It is an important feature of the apparatus as described that in the conventional testing equipment the basic components are already included, such as a trigger circuit and the transmitter and launch circuit to operate the transducer, an amplifier for the detected signal as well as gating circuitry for receiving echo signals limited to a particular interval, such as interval period 8 as mentioned above. The inventive system (i.e., the realization of the inventive concept) can be carried out through supplementing circuitry which establishes additional time intervals for purposes of recognizing under certain circumstances the rear wall echo as a defect signal.

The invention is not limited to the embodiments described above, but all changes and modifications thereof not constituting departures from the spirit and scope of the invention, are intended to be included.

We claim:

1. A method for nondestructive testing of structural material having front and rear surfaces and under utilization of ultrasonic test pulses set into the front surface and under further utilization of echoes being detected as return signals emerging from said front surface, comprising the steps of:

providing a first gating and detection period for echo signals which covers at least a period in which a rear wall echo will appear;

detecting any echo signal that occurs within said period, the detected echo signal may be a defect echo or a true rear wall echo and using such detection for generating a second gating and detection period; and detecting a rear wall echo that occurs in the second gating period as an indication of the presence of a defect.

2. In an apparatus for nondestructive testing of structural material having front and rear surfaces, the apparatus including transducing means for launching ultrasonic test pulses into the front surface and for receiving return signals emerging from the front surface and converting the return signals into electrical signals, the combination comprising:

a first threshold circuit connected to receive the electrical signals as detected by transducing means;

a second threshold circuit also connected to receive the electrical signals provided by the transducing means but having a higher threshold level than the first threshold circuit.

first, timed gating means connected to receive an output from the first threshold circuit during a period in which a rear surface echo will occur and in which also echoes from any defect near that rear surface may occur;

circuit means for generating a gating signal in response to any signal that passed through the first gating means;

second gating means connected to be responsive to outputs from the second threshold means and for the duration of the gating signal as provided by the circuit means; and means connected to be responsive to any output that has passed the second gating means and registering same as a defect indication.

3. In an apparatus as in claim 2 including further means connected for inhibiting plural responses to the circuit means in case more than one echo is detected by the first gating means.

4. A method for nondestructive testing of structural material of variable thickness having front and rear surfaces of variable distance accordingly and under utilization of ultrasonic test pulses set into the front surface and under further utilization of echoes being detected as return signals emerging from said front surface, comprising the steps of:

providing a first gating and detection period for echo signals which covers a period in which a rear wall echo will not appear;

providing a second gating and detection period for echo signals which covers a period in which any rear wall echo will appear;

first detecting any echo signal that occurs within said second period, the detected echo signal may be a defect echo or a ture rear wall echo and using such detection for generating a third gating and detection period to begin after the latter detection, the beginning being variable accordingly depending upon the occurence of the echo; and second detecting a rear wall echo if occurring in the third gating period as an indication of the presence of a defect.

5. A method as in claim 4, wherein the first detecting step is carried out under selection of a particular threshold which such echo signal has to exceed, and such second detecting step is carried out under utilization of a threshold higher than the particular threshold.

* * * * *